(12) United States Patent
Mizobe

(10) Patent No.: US 10,956,111 B2
(45) Date of Patent: Mar. 23, 2021

(54) INFORMATION PROCESSING APPARATUS, INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventor: Hideaki Mizobe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 3 days.

(21) Appl. No.: 16/149,438

(22) Filed: Oct. 2, 2018

(65) Prior Publication Data

US 2019/0107989 A1    Apr. 11, 2019

(30) Foreign Application Priority Data

Oct. 6, 2017 (JP) .............................. JP2017-196055

(51) Int. Cl.
  *G06F 3/14* (2006.01)
  *G09G 5/38* (2006.01)
  (Continued)

(52) U.S. Cl.
  CPC ............ *G06F 3/1446* (2013.01); *G06F 9/451* (2018.02); *G09G 5/14* (2013.01); *G09G 5/373* (2013.01); *G09G 5/38* (2013.01); *G16H 30/20* (2018.01); *G16H 40/63* (2018.01); *G06F 3/0482* (2013.01); *G06F 3/04845* (2013.01); *G09G 2340/04* (2013.01); *G09G 2340/0464* (2013.01); *G09G 2354/00* (2013.01); *G09G 2380/08* (2013.01)

(58) Field of Classification Search
  None
  See application file for complete search history.

(56) References Cited

U.S. PATENT DOCUMENTS 5,835,090 A * 11/1998 Clark ....................... G09G 5/14
                                                   715/764
8,330,733 B2 * 12/2012 Petschnigg ........... G06F 1/1647
                                                   345/173
(Continued)

FOREIGN PATENT DOCUMENTS

JP           2015-38746 A      2/2015

OTHER PUBLICATIONS

Nacenta et al "E-conic: a Perspective-Aware Interface for Multi-Display Environments", UIST'07, Oct. 2007. (Year: 2007).*

(Continued)

*Primary Examiner* — Patrick F Valdez
(74) *Attorney, Agent, or Firm* — Canon U.S.A., Inc. IP Division

(57) ABSTRACT

An information processing apparatus that controls a display on one or more display apparatuses includes a determination unit that determines whether at least a portion of a display part in a window displayed in a displayable region of the display apparatus is arranged on a position outside the displayable region and a changing unit that changes, based on a result of the determination, at least the position of the display part or the size of the display part or the size of a region where the display part is displayed, such that at least the portion of the display part is not arranged on a position outside the displayable region.

12 Claims, 15 Drawing Sheets

(51) Int. Cl.
    *G09G 5/373*      (2006.01)
    *G09G 5/14*       (2006.01)
    *G16H 30/20*      (2018.01)
    *G16H 40/63*      (2018.01)
    *G06F 9/451*      (2018.01)
    *G06F 3/0482*     (2013.01)
    *G06F 3/0484*     (2013.01)

(56) References Cited

U.S. PATENT DOCUMENTS

2014/0325432 A1\* 10/2014 Frederickson .......... G06F 9/451
                                                                 715/788
2015/0145779 A1\* 5/2015 Kouda ................... G09G 5/003
                                                                  345/168

OTHER PUBLICATIONS

Mackinlay et al, "Wideband Displays: Mitigating Multiple Monitor Seams", CHI 2004, pp. 1521-1524, 2004. (Year: 2004).\*

\* cited by examiner

INFORMATION PROCESSING APPARATUS, INFORMATION PROCESSING METHOD, AND NON-TRANSITORY COMPUTER-READABLE STORAGE MEDIUM

BACKGROUND

Field

The present disclosure relates to an information processing apparatus, an information processing method, and a non-transitory computer-readable storage medium.

Description of the Related Art

In some medical institutions and facilities, radiologists examine medical images captured by medical image capturing apparatuses to examine the extent and progress of a disease of a patient, which is a medical practice generally called radiologic interpretations. In recent years, radiologic interpretations are conducted by displaying digitalized medical images on monitors with high definition and high luminance. Many medical institutions and facilities conduct radiologic interpretations using a method in which two or more monitors are placed next to each other to display medical images captured at different time points on the respective monitors for the purpose of examining the progress of a disease. This display form is employed for several reasons. For example, the number of monitors is increased so that the display region per medical image is enlarged to enable more detailed examination of the medical images. The monitors though, especially liquid crystal monitors, have a problem that displayed colors can appear differently depending on the viewing angle. Thus, a plurality of monitors is arranged vertically to the line of sight of a radiologist, instead of displaying medical images next to each other on a large monitor, so that the above-described problem associated with the viewing angle is reduced to enable accurate radiologic interpretations.

In the case of using a plurality of monitors, a control (e.g., window, icon, etc. also referred to as "graphical user interface (GUI) part") of a GUI displayed on one of the monitors can be moved onto another monitor. Japanese Patent Application Laid-Open No. 2015-38746 discusses a conventional technique for moving a control on an electronic device including a plurality of monitors. Specifically, when a control is moved from a first monitor to a second monitor, if the control is moved beyond the edge of the first monitor, a portion of the control is not displayed on the first monitor while the portion of the control is displayed on the second monitor.

SUMMARY

According to an aspect of the present disclosure, an information processing apparatus configured to display a window over a first display apparatus and a second display apparatus includes a determination unit configured to determine whether a display part in the window is arranged over a first displayable region of the first display apparatus and a second displayable region of the second display apparatus, and a changing unit configured to change, based on a result of the determination, at least a position of the display part, a size of the display part, or a size of a region where the display part is to be arranged, such that the display part is prevented from being arranged over the first displayable region and the second displayable region.

Further features will become apparent from the following description of exemplary embodiments with reference to the attached drawings.

DESCRIPTION OF THE EMBODIMENTS

Figure 1:
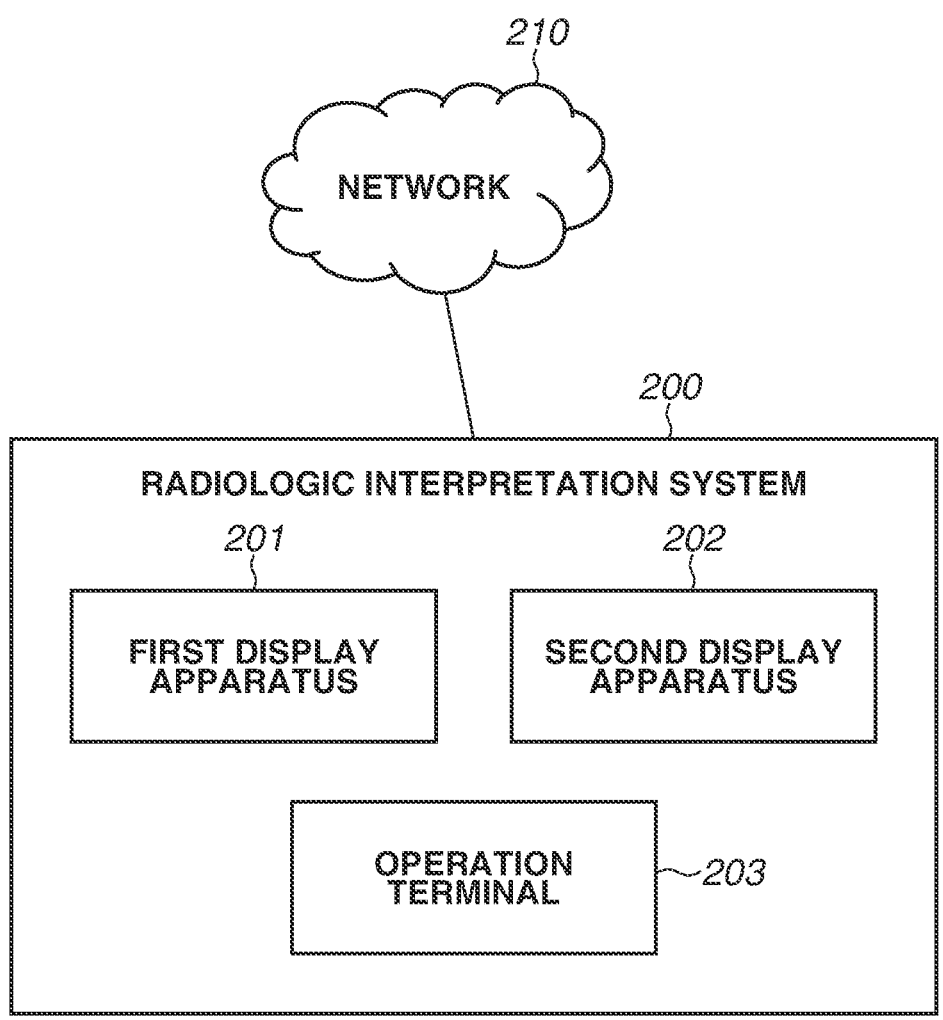
FIG. 1 illustrates an example of a configuration of a radiologic interpretation system according to a first exemplary embodiment.

With the technique discussed in Japanese Patent Application Laid-Open No. 2015-38746, a portion of a control of a graphical user interface (GUI) is drawn over the border between monitors. Consequently, the control appears to be divided or only a portion of the control is visible in the field of view of the user, causing a problem that the type of the control is difficult to identify.

In response to the problem, the technique disclosed herein is directed to preventing a situation where at least a portion of a display part is arranged at a position outside a displayable region of a display apparatus.

An aspect of the present disclosure is not limited to the foregoing, and producing an advantage that is derived from a configuration described below and cannot be produced by a conventional technique is also positioned as another aspect of the disclosure.

Information processing apparatuses according to various exemplary embodiments of the disclosure will be described in detail below with reference to the attached drawings. It should be noted that the illustrated examples are not intended to limit the scope of the disclosure.

First, terms that are necessary to describe a first exemplary embodiment will be described below.

As used herein, the term "operation terminal" (information processing apparatus) refers to an apparatus including a device such as a mouse, keyboard, and/or touch panel with which a user provides an instruction to the operation terminal. Specifically, the operation terminal corresponds to an example of an information processing apparatus configured to display a window over a first display apparatus and a second display apparatus. Software programmed to cause various types of processing described below to operate is installed in the operation terminal, and the program is executed and data is input and output as needed. Examples of the operation terminal include a personal computer (hereinafter, "PC"), work station, tablet PC, personal digital assistant (PDA), and smartphone.

As used herein, the term "display apparatus" (display unit) refers to an apparatus that is connected to an electronic calculation device (i.e., operation terminal), such as a PC or work station, and displays screen outputs and three-dimensional outputs drawn by the software running on the electronic calculation device. Examples include a liquid crystal monitor, cathode ray tube (CRT) display, and three-dimensional projection device.

As used herein, the term "network" refers to an interface connecting the apparatuses. Examples include a private line, local area network (hereinafter, "LAN"), wireless LAN, and Internet line.

As used herein, the term "medical image capturing apparatus" refers to an apparatus configured to capture images for use in medical diagnosis. Examples include a magnetic resonance imaging (also referred to as "MRI") apparatus, X-ray computer tomographic (also referred to as "CT") imaging apparatus, and positron emission tomographic (also referred to as "PET") imaging apparatus.

As used herein, the term "picture archiving and communication system" (PACS) refers to an image saving and communication system. PACS is a system configured to receive and save medical images captured by medical image capturing apparatuses and transmit medical images in response to a request from a connected apparatus. PACS includes a database that stores received medical images in association with various types of data, such as imaged patient information and imaging time. In general, PACS is connected to a network to receive and transmit medical images and various types of associated data in response to requests from other systems.

As used herein, the term "control" refers to an element constituting a GUI, and examples include a window, button, check box, radio button, combo box, scroll bar, text box, slider, icon, image, and text label. The controls can execute predetermined functions.

Next, the drawings necessary for describing the present exemplary embodiment will be described below.

FIG. 1 illustrates a radiologic interpretation system 200 in which medical image display software 100 according to the present exemplary embodiment is installed to be used by the radiologic interpretation system. The radiologic interpretation system 200 includes a first display apparatus 201, a second display apparatus 202, and an operation terminal 203, where the operation terminal 203 is connected to a network 210. While the number of display apparatuses of the present exemplary embodiment is two for description purposes, the present exemplary embodiment is implementable with one display apparatus or more than two display apparatuses. The medical image display software 100 is installed in the operation terminal 203. The medical image display software 100 receives medical images input from other systems, such as a PACS, via the network 210 connected to the operation terminal 203. The medical image display software 100 configures a GUI to enable the user of the radiologic interpretation system 200 to conduct radiologic interpretations. The medical image display software 100 displays the GUI on one or both of the first display apparatus 201 and the second display apparatus 202 based on the context, such as a user operation of the operation terminal 203 or a predetermined action.

Figure 2:
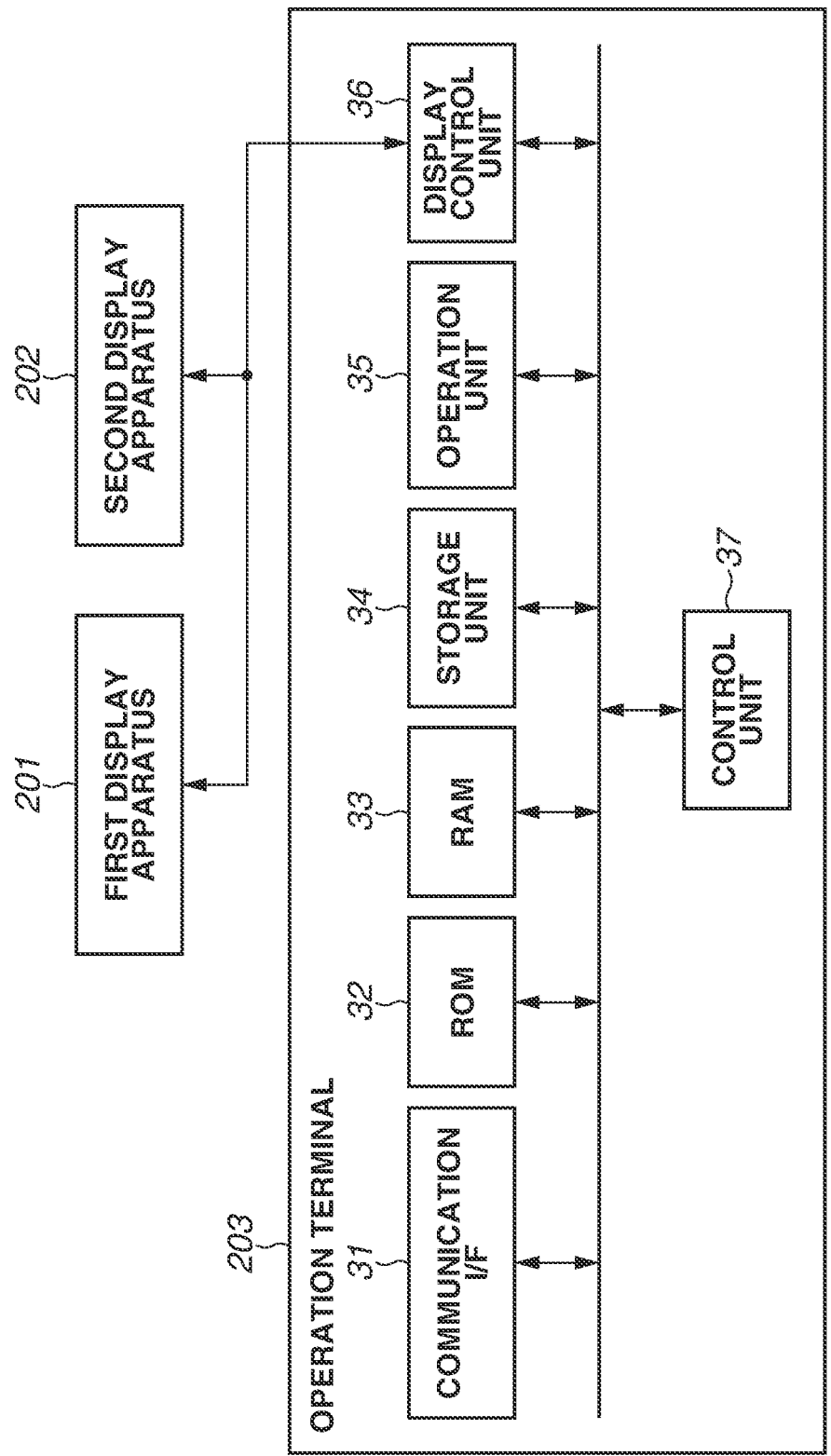
FIG. 2 is a block diagram illustrating an example of a hardware configuration of an operation terminal according to the first exemplary embodiment.

FIG. 2 illustrates an example of a hardware configuration of the operation terminal 203 according to the present exemplary embodiment. The hardware configuration of the present exemplary embodiment is a mere example and an image processing apparatus including hardware other than the illustrated hardware can be employed.

The operation terminal 203 includes a communication interface (I/F) 31 (communication unit), a read-only memory ROM 32, a random-access memory (RAM) 33, a storage unit 34, an operation unit 35, a display control unit 36, and a control unit 37.

The communication I/F 31 (communication unit) includes a LAN card and realizes communication between an external apparatus (e.g., PACS, etc.) and the operation terminal 203 via the network 210. The ROM 32 includes a non-volatile memory and stores various programs. The RAM includes a volatile memory and temporarily stores various types of information as data. The storage unit 34 includes a hard disk drive (HDD) and stores various types of information as data. The operation unit 35 includes a keyboard, mouse, and touch panel and inputs user (e.g., doctor) instructions to various apparatuses.

The display control unit 36 controls the display of images on the first display apparatus 201 and the second display apparatus 202. Specifically, the display control unit 36 corresponds to, for example, a graphic controller (graphics processing unit (GPU), etc.). The control unit includes a central processing unit (CPU) and comprehensively controls processing executed at the operation terminal 203. The control unit 37 operates as a function unit that executes the functions illustrated in FIG. 3 described below.

Figure 3:
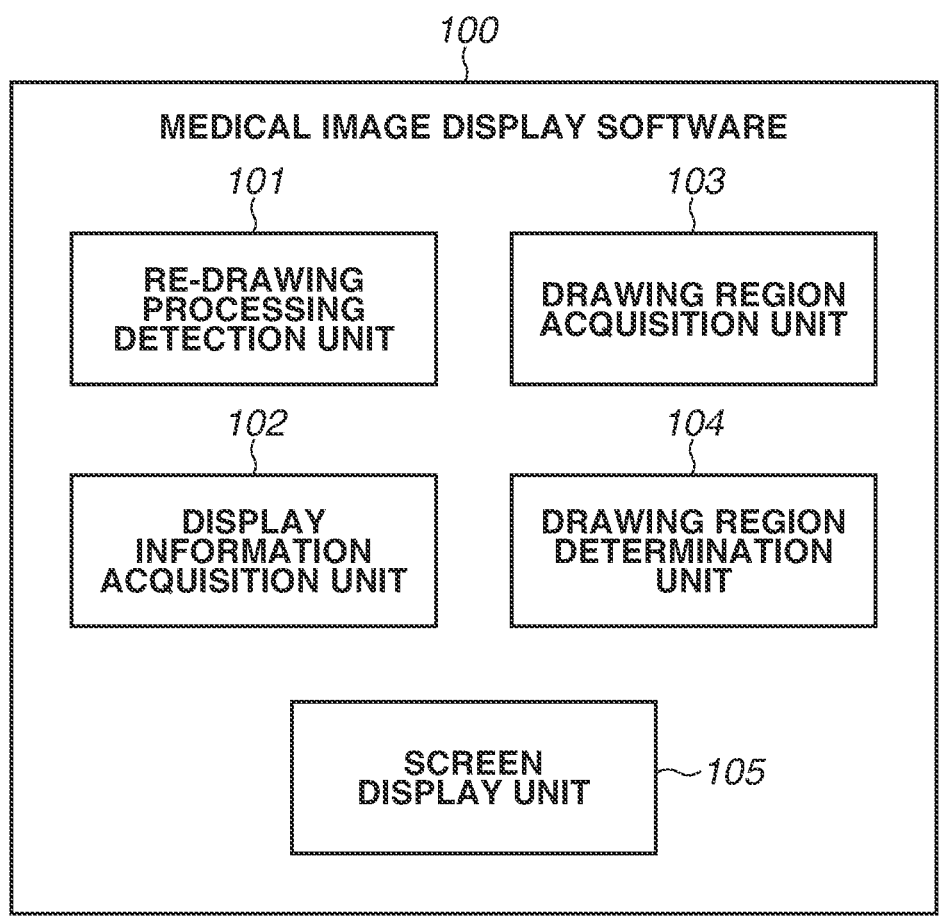
FIG. 3 is a block diagram illustrating an example of a functional configuration of medical image display software according to the first exemplary embodiment.

FIG. 3 is a block diagram illustrating a functional configuration according to the present exemplary embodiment that is implemented on the operation terminal 203 according to the present exemplary embodiment. If the medical image display software 100 is installed in the operation terminal 203, the control unit 37 can execute the functions illustrated in FIG. 3. In the following description, for convenience, various types of processing executed by the control unit 37 will be described as being executed by the medical image display software 100. For example, the description "the control unit 37 of the operation terminal 203 in which the medical image display software 100 is installed executes processing" will be simplified to the description "the medical image display software 100 executes processing".

A re-drawing processing detection unit 101 detects a GUI re-drawing instruction that triggers execution of step S101 described below. A display information acquisition unit 102 acquires a display coordinate needed in step S101 described below. A drawing region acquisition unit 103 acquires a control coordinate needed in step S102 described below. A drawing region determination unit 104 derives a definite drawing region needed in step S104 described below. A screen display unit 105 performs GUI drawing in step S104 described below. The functions can be integrated together or can be configured by a plurality of software groups that communicate information needed by each function.

Figure 4:
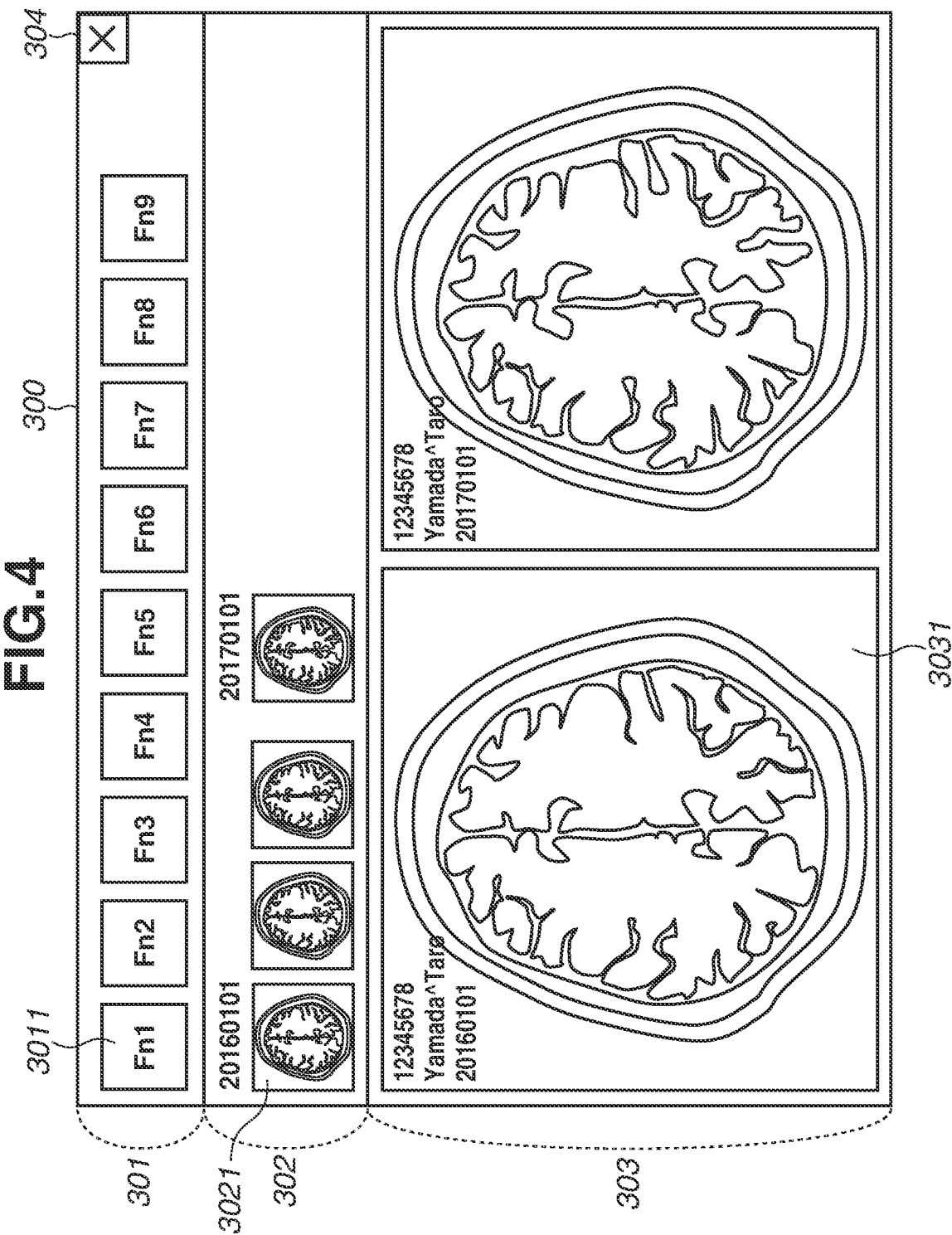
FIG. 4 illustrates an example of a configuration of a graphical user interface (GUI) of the medical image display software according to the first exemplary embodiment.

FIG. 4 illustrates an example of a GUI displayed on a display apparatus by the medical image display software 100 according to the present exemplary embodiment. The GUI illustrated in FIG. 4 is a mere example, and the present exemplary embodiment is not limited to the above-described GUI configuration. The GUI configuration includes a window 300 including approximately three sections on top of another, which are a function button region 301, a thumbnail image region 302, and an examined image region 303 in this order from the top. In the function button region 301, function buttons (rectangle regions Fn1, Fn2, . . . , Fn9) illustrated as function buttons 3011 are left-justified and displayed. The number of function buttons is not limited to the nine illustrated in FIG. 4 and can be increased or decreased based on the number of functions to be assigned to the function buttons.

In general radiologic interpretations, it is improvement in work efficiency is needed to enable a prompt response to the patient, reduce user fatigue, and prevent misdiagnoses. Thus, medical image display software for use in general radiologic interpretations, as well as the medical image display software in the present exemplary embodiment, often include a large number of functions to assist radiologic interpretations so that medical images are examined in detail and accurately in a short time. The functions for assisting in the radiologic interpretations can be assigned to the function buttons of the medical image display software 100 to enable the user to use the functions promptly and with ease. For example, the user can operate a device such as a mouse connected to the operation terminal to input an instruction to execute the functions so that the user can use the functions.

Figure 5:
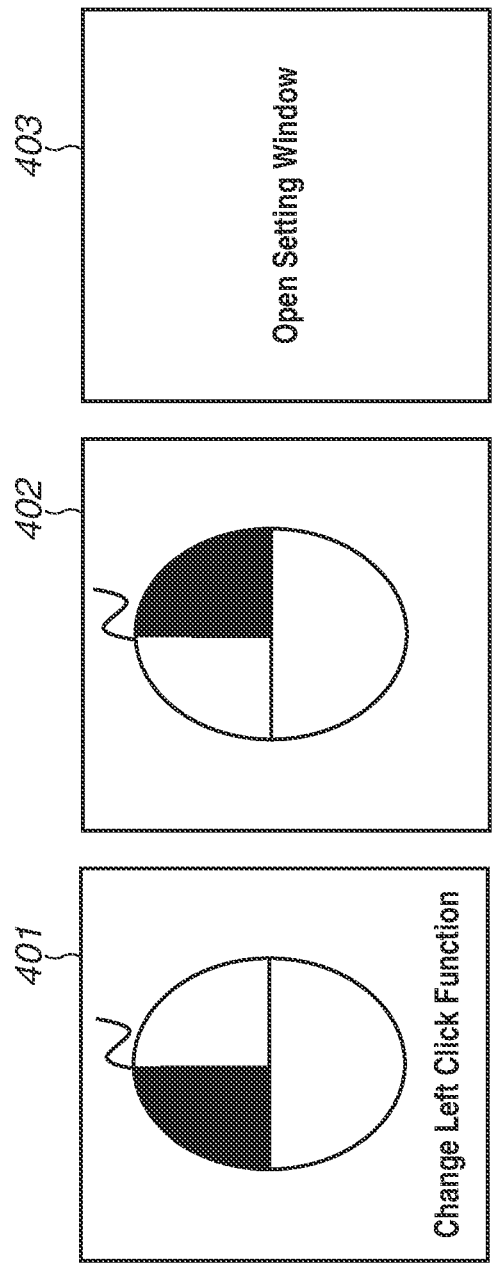
FIG. 5 illustrates an example of function buttons of the medical image display software according to the first exemplary embodiment.

Various functions are assigned to the function buttons. There are many examples, including the function of adjusting the display colors of medical images, the function of measuring lesions in medical images, the function of changing the number of medical images to be displayed in the examined image region 303 and how the medical images are arranged, and the function of displaying a screen for the settings of the medical image display software 100. In the drawing region where the function buttons are arranged, it is desirable to provide a drawing that presents an effect of each assigned function to the user. Thus, for example, an icon image representing an effect of a function, e.g., a function button display example 402 in FIG. 5, can be displayed instead of displaying text as in the drawing region of the function buttons in FIG. 4. A character string representing an effect of a function, as in a function button display example 403, can be displayed, or a combination of an icon image and a character string can be displayed as in a function button display example 401.

Figure 6:
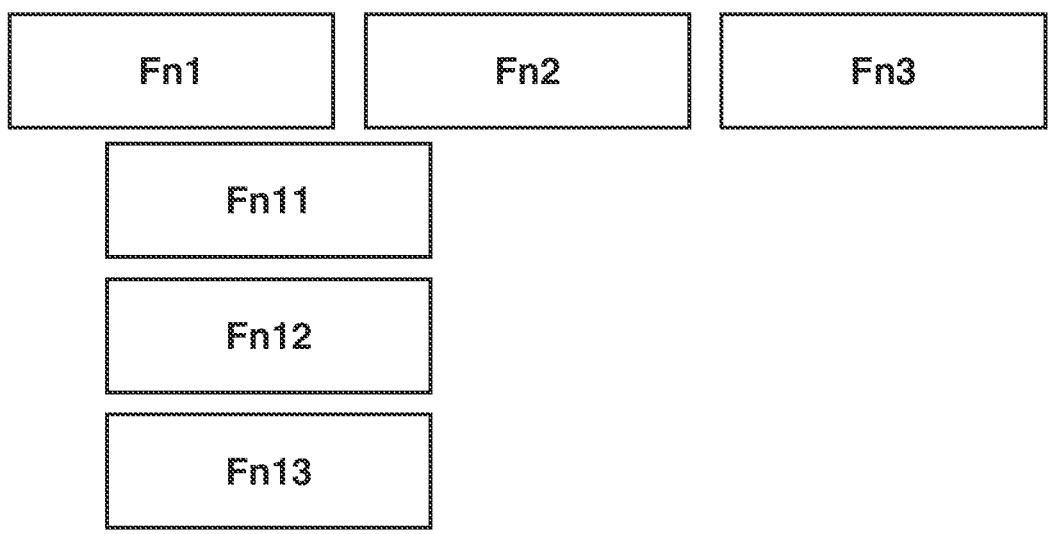
FIG. 6 illustrates an example of derivative function buttons of the medical image display software according to the first exemplary embodiment.

As described above, the medical image display software 100 includes a large number of functions, and even if only frequently-used functions are selected and assigned to the function buttons, it is sometimes impossible to display all in the window 300. Thus, the medical image display software 100 also employs a display form where, when a user operates a function button, related function buttons (hereinafter, "derivative function buttons") are newly displayed so that the user can operate a function button relating to a function to be used from among the displayed function buttons. Specifically, the display form is such that, if the function button Fn1 is operated, derivative function buttons Fn11, Fn12, and Fn13 are newly displayed, as illustrated in FIG. 6, so that the user can operate a function button relating to the function that the user desires to use from among the displayed function buttons. The derivative function buttons are not continually displayed, and if the user operates one of the controls constituting the window 300 including the derivative function buttons, the derivative function buttons are hidden.

Referring back to FIG. 4, in the thumbnail image region 302, thumbnail images such as thumbnail images 3021 corresponding to the medical images input by the medical image display software 100 are displayed side by side. In the examined image region 303 medical images to be examined by the user are displayed, such as an examined image 3031. The examined image region 303 is a region to display an enlarged image on different display apparatuses. Examples of a method of selecting a medical image to be displayed in the examined image region 303 include a method in which the user selects a thumbnail image corresponding to a desired medical image from thumbnail images displayed in the thumbnail image region 302. For example, if the user operates the mouse connected to the operation terminal 203 to drag and drop the thumbnail image corresponding to the medical image to be examined from the thumbnail image region 302 to the examined image region 303, the medical image is displayed in the examined image region 303. An end button 304 is a button that is operated by the user to end the medical image display software 100.

Figure 7:
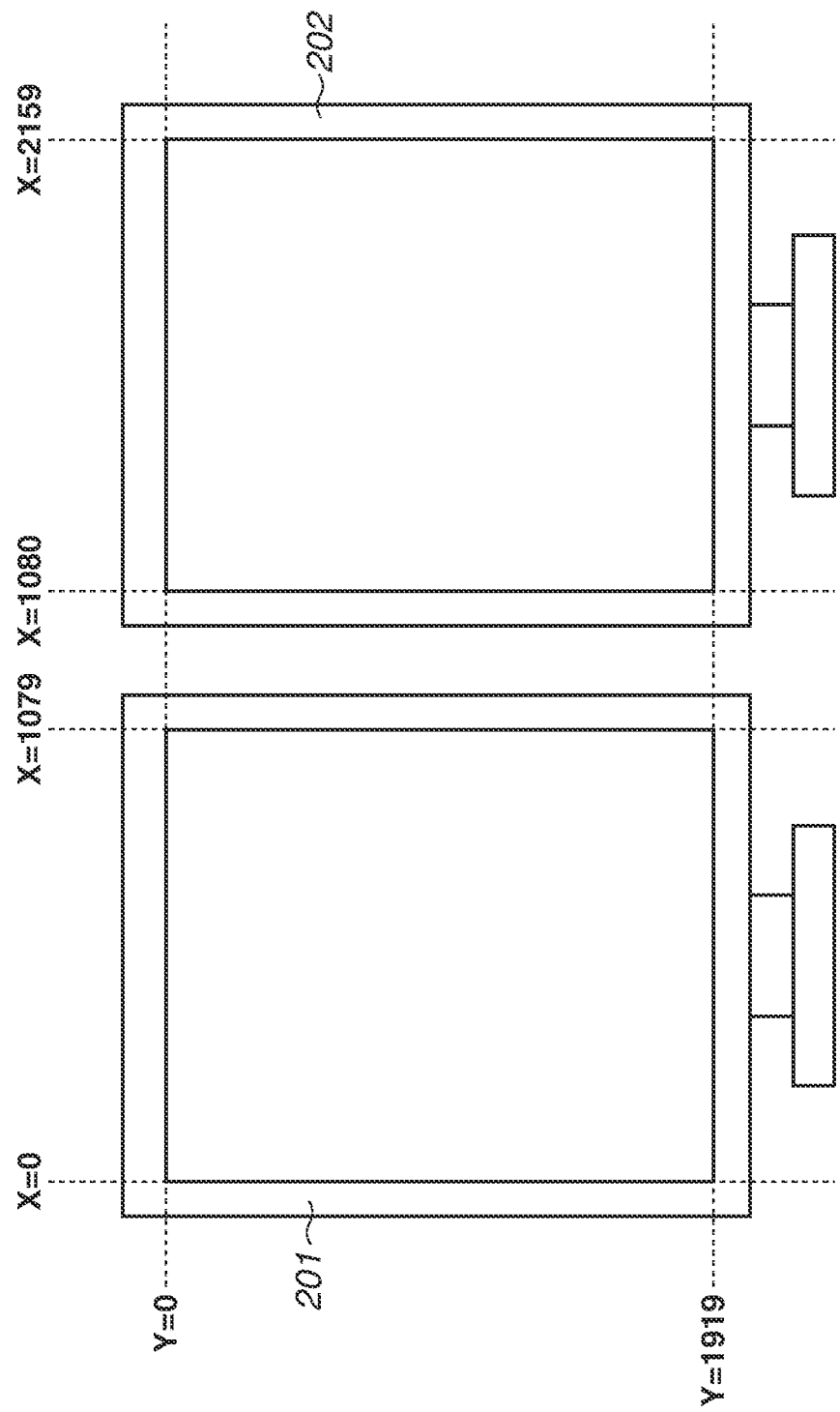
FIG. 7 illustrates an example of display coordinates of the radiologic interpretation system according to the first exemplary embodiment.

FIG. 7 illustrates display coordinates of the first display apparatus 201 and the second display apparatus 202 that constitute the radiologic interpretation system 200 according to the present exemplary embodiment. The term "display coordinate" refers to coordinate information about a virtual layout of the displayable regions that is set regardless of the physical location of the display apparatus. As illustrated in FIG. 7, the first display apparatus 201 and the second display apparatus 202 are multi-monitors. The display coordinates are managed by the operation terminal 203, and the medical image display software 100 can acquire the display coordinates from the operation terminal 203 as needed. To simplify the description, the elements constituting the GUI are drawn on a two-dimensional plane, and the plane will be described using an XY-coordinate system. In the XY-coordinate system, the direction in which the X-coordinate increases is a rightward direction, the direction in which the Y-coordinate increases is a downward direction, and the unit is pixel. The GUI coordinate system controllable by the medical image display software 100 can be extended to three-dimensional system.

If the display coordinate is determined, the screen resolutions of the respective display apparatuses and the virtual relative positional relationship between the display apparatuses are determined. Specifically, as illustrated in FIG. 7, the display coordinates of the first display apparatus 201 are (X, Y)=(0, 0) for the upper left and (X, Y)=(1079, 1919) for the lower right. The display coordinates of the second display apparatus 202 are (X, Y)=(1080, 0) for the upper left and (X, Y)=(2159, 1919) for the lower right. Specifically, it is understood that the first display apparatus 201 and the second display apparatus 202 each have a horizontal screen resolution of 1080 pixels and a vertical screen resolution of 1920 pixels. It is also understood that virtually, the first display apparatus 201 and the second display apparatus 202 are displayed next to each other.

Figure 8:
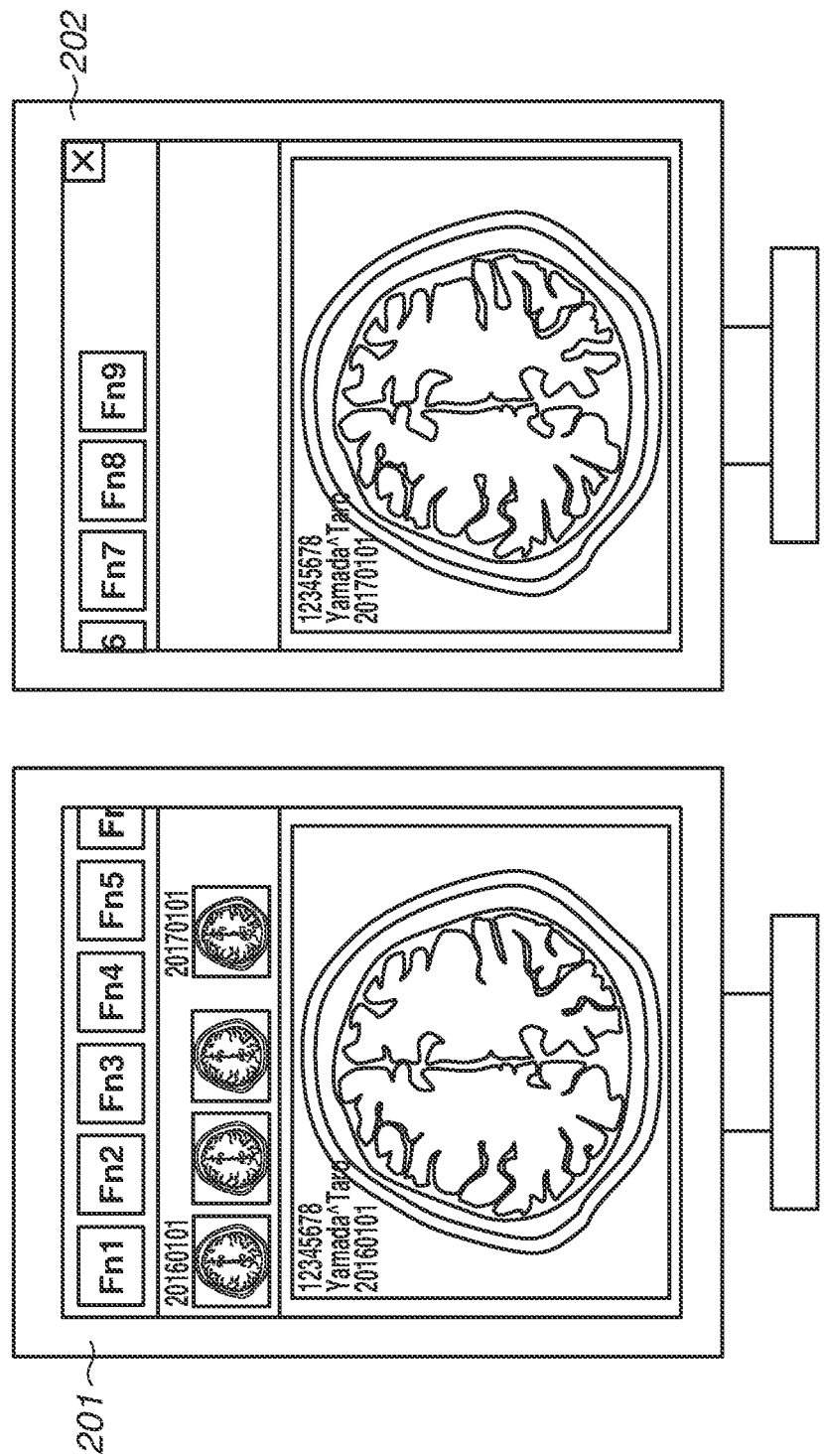
FIG. 8 illustrates an example of a state of conventional medical image display software.

FIG. 8 illustrates a window of the virtual medical image display software of convention medical image display software that does not include the GUI drawing method and the program according to the present exemplary embodiment. In FIG. 8, elements that are similar to those of the medical image display software 100 are included. In the case where the GUI drawing method and the program according to the present exemplary embodiment are not provided, the drawing region of the function button Fn6 is divided into two regions, left and right regions, at the portion corresponding to the function button region 301 in FIG. 4, and the two regions are respectively displayed on the first display apparatus 201 and the second display apparatus 202. In other words, a display apparatus in general includes a display apparatus frame outside a displayable region, so that the function button Fn6 appears to be physically separated in the field of vision of the user, making it difficult for the user to instantly recognize the type of the function button. When the above-described situation occurs while a radiologic interpretation is performed, if the type of the control is difficult to recognize, it can be especially difficult to make a diagnosis promptly or an erroneous operation can be performed to cause a misdiagnosis. A flat design is one of the GUI design methods that has become mainstream in recent years. In the flat design, frame lines of controls are not drawn and the foreground color of the controls and the background color of the surrounding area are the same, so that it can sometimes be difficult to discriminate the border between one control and another control. Thus, in the case where the control appears to be divided as described above, the user can erroneously recognize the divided regions as different controls.

Figure 9:
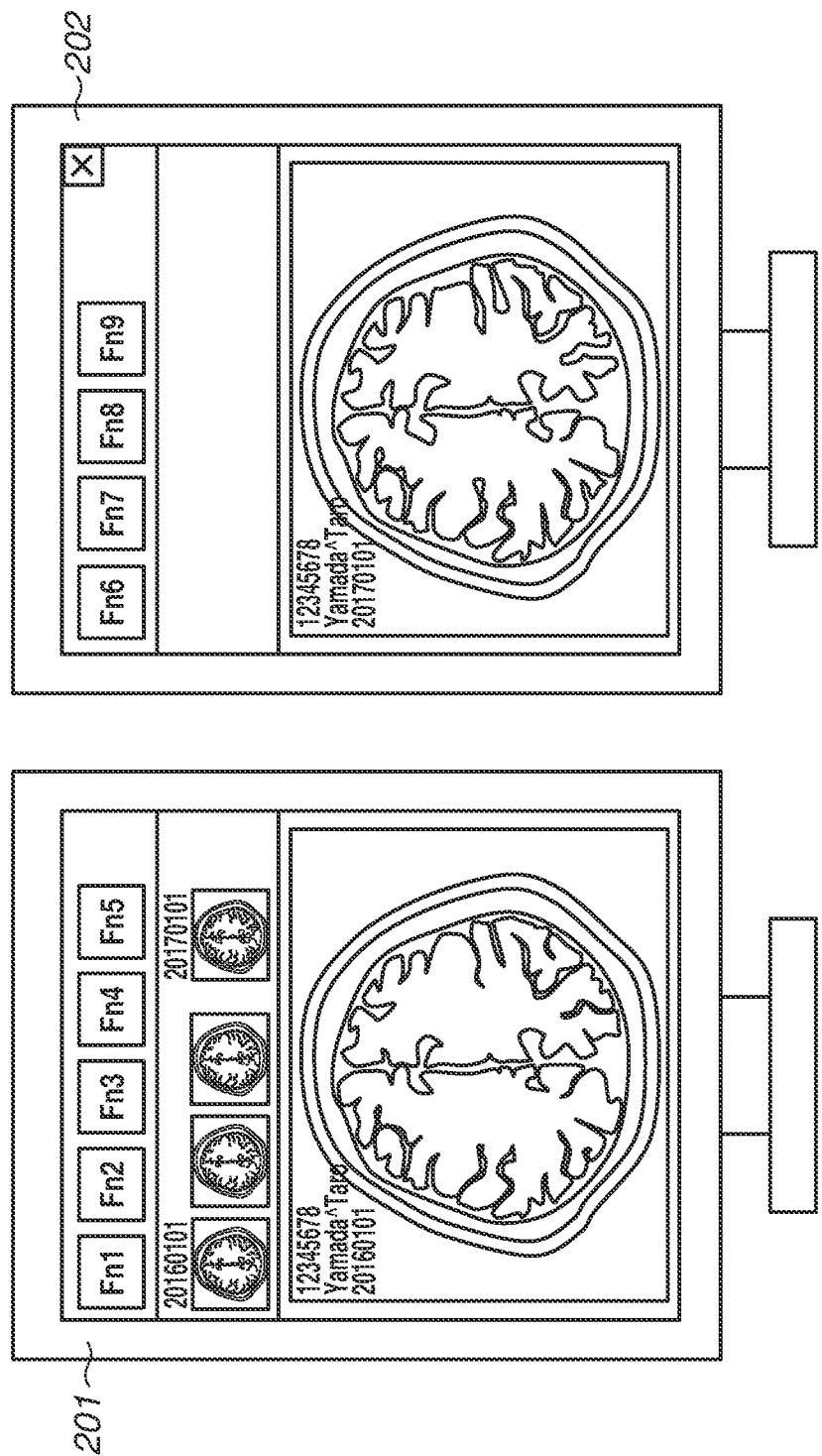
FIG. 9 is a first view illustrating an example of a state of the medical image display software according to the first exemplary embodiment.

FIG. 9 illustrates the window 300 that is maximized and displayed on the first display apparatus 201 and the second display apparatus 202 by the medical image display software 100 including the GUI drawing method and the program according to the present exemplary embodiment. The medical image display software 100 adjusts, as needed, the coordinates at which the respective function buttons are to be drawn, thereby preventing the function buttons from being drawn over ends (hereinafter, "screen end") of the displayable regions of the display apparatuses. Specifically, this prevents the function buttons from appearing to be divided in the field of vision of the user. Hereinafter, a control that is a target of drawing coordinate adjustment, such as the function buttons in the present exemplary embodiment, will be referred to as "drawing region adjustment target control". While the drawing region adjustment target control is the function buttons in the medical image display software 100 according to the present exemplary embodiment, the same is also applicable to thumbnail images and examined images. In addition to the case of the medical image display software 100 according to the present exemplary embodiment, in the case of general software including a GUI, it is suitable to adjust the drawing coordinates of controls to prevent the controls from being drawn over the screen ends in order to solve similar problems.

Figure 10:
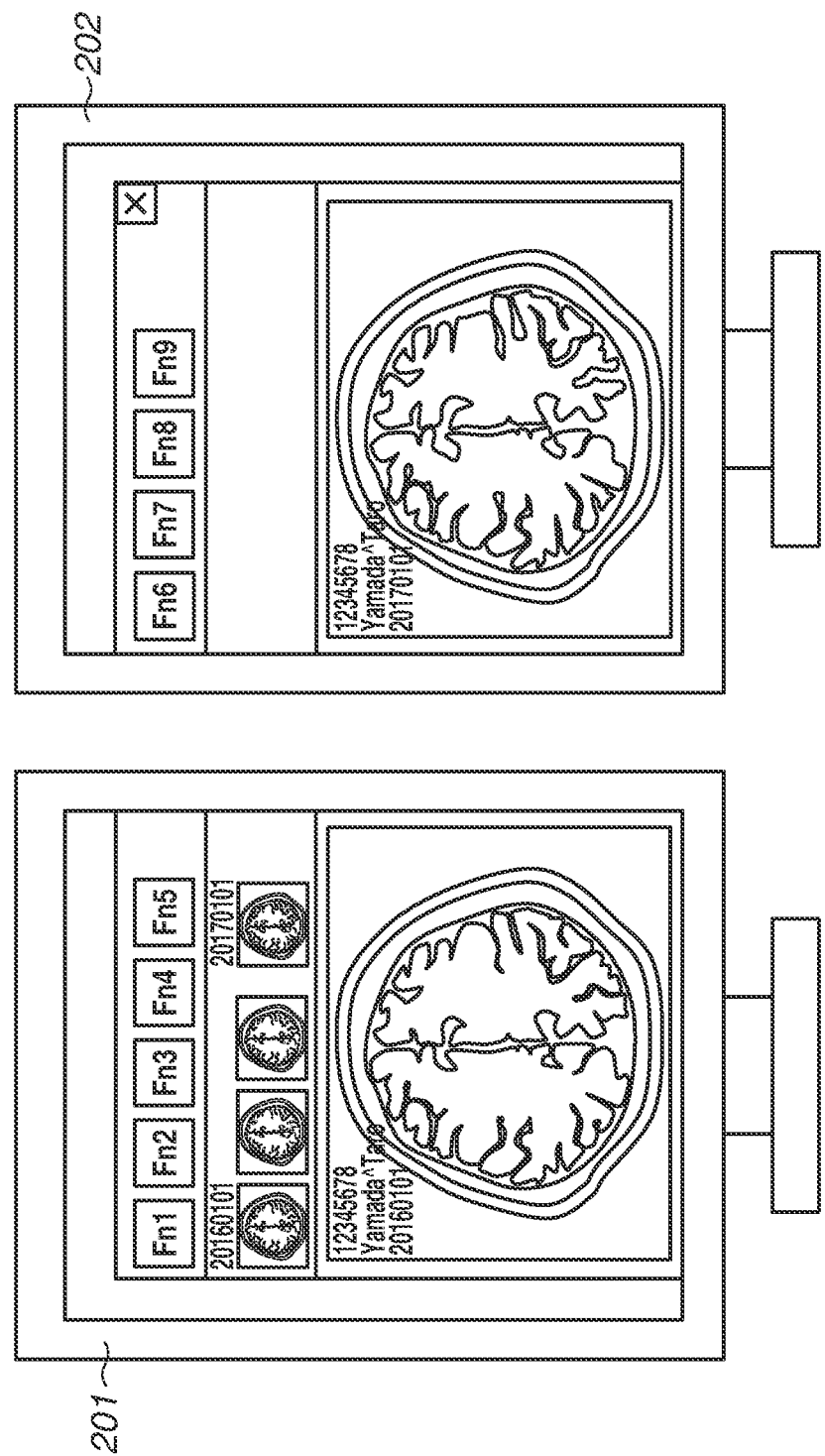
FIG. 10 is a second view illustrating an example of a state of the medical image display software according to the first exemplary embodiment.

FIG. 10 illustrates the window 300 of the medical image display software 100 including the GUI drawing method and the program according to the present exemplary embodiment, which is displayed on the first display apparatus 201 and the second display apparatus 202. FIG. 10 is different from FIG. 9 in that the window 300 is not maximized on the first display apparatus 201 and the second display apparatus 202. Specifically, according to the present exemplary embodiment, the coordinates at which the function buttons are drawn are adjustable to prevent the function buttons from being displayed over the screen ends, regardless of whether the window 300 is maximized.

Figure 11:
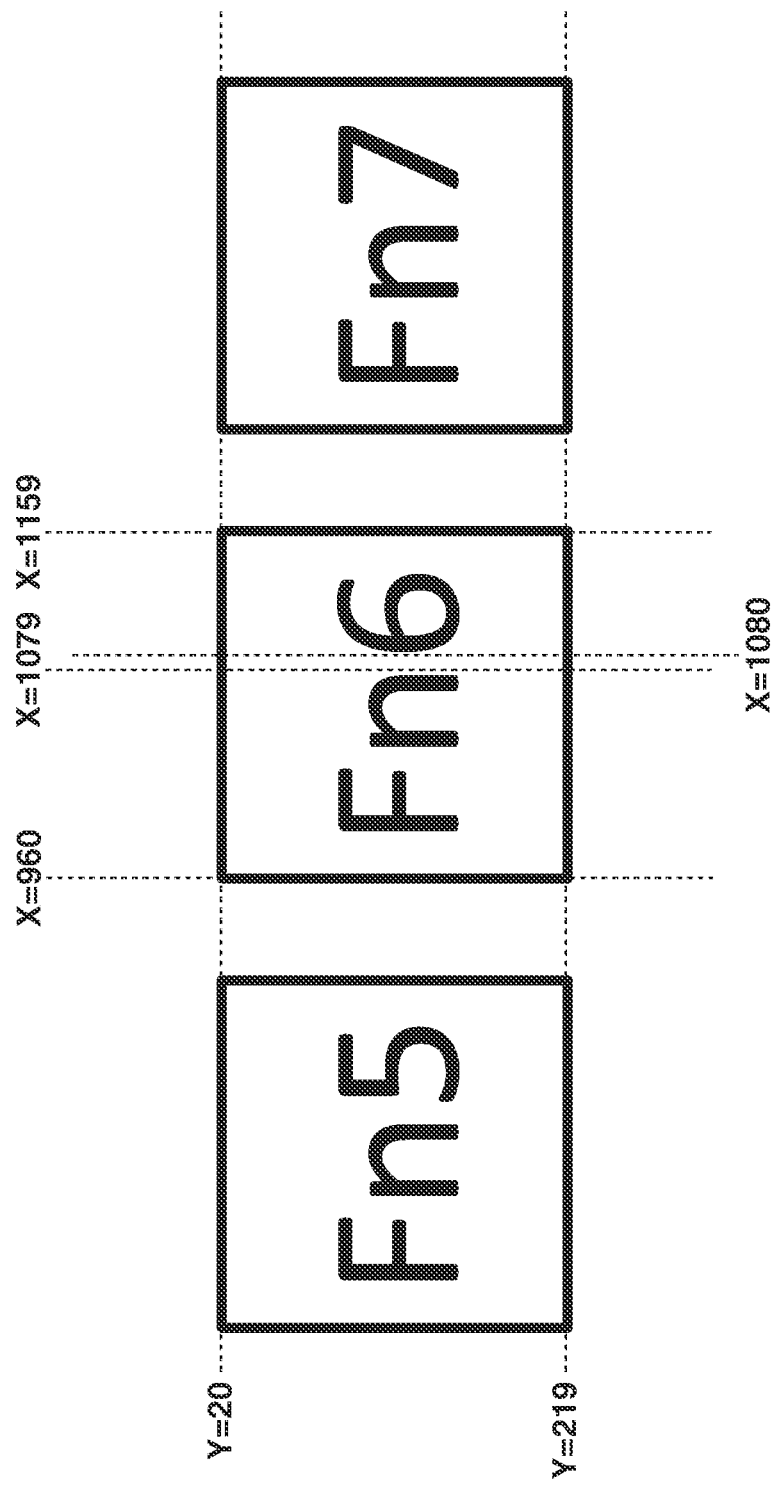
FIG. 11 illustrates an example of a function button drawing region according to the first exemplary embodiment.

FIG. 11 illustrates control coordinates with respect to the function button Fn6 of the window 300. The control coordinates refer to the coordinates that indicate the position at which a control is to be drawn in the display coordinates. Specifically, in FIG. 11, the function button Fn6, which is a control, is drawn in the region having the upper left at (X, Y)=(960, 20) and the lower right at (X, Y)=(1159, 219) in the display coordinates. The control coordinates are irrelevant to whether the corresponding control is actually drawn and displayed on the display apparatuses and visible to the user. That is, since the controls are under the management of the GUI controlled by the medical image display software 100, it is possible to acquire the control coordinates of a control that is currently not displayed on the display apparatuses but is to be drawn. Hereinafter, a rectangle region in which a control is surrounded by coordinates corresponding to the upper left and the lower right, i.e., the region where the control is to be drawn, will be referred to as "drawing region".

A process according to the present exemplary embodiment will be described below with reference to the flowcharts in FIGS. 12 and 13.

Figure 12:
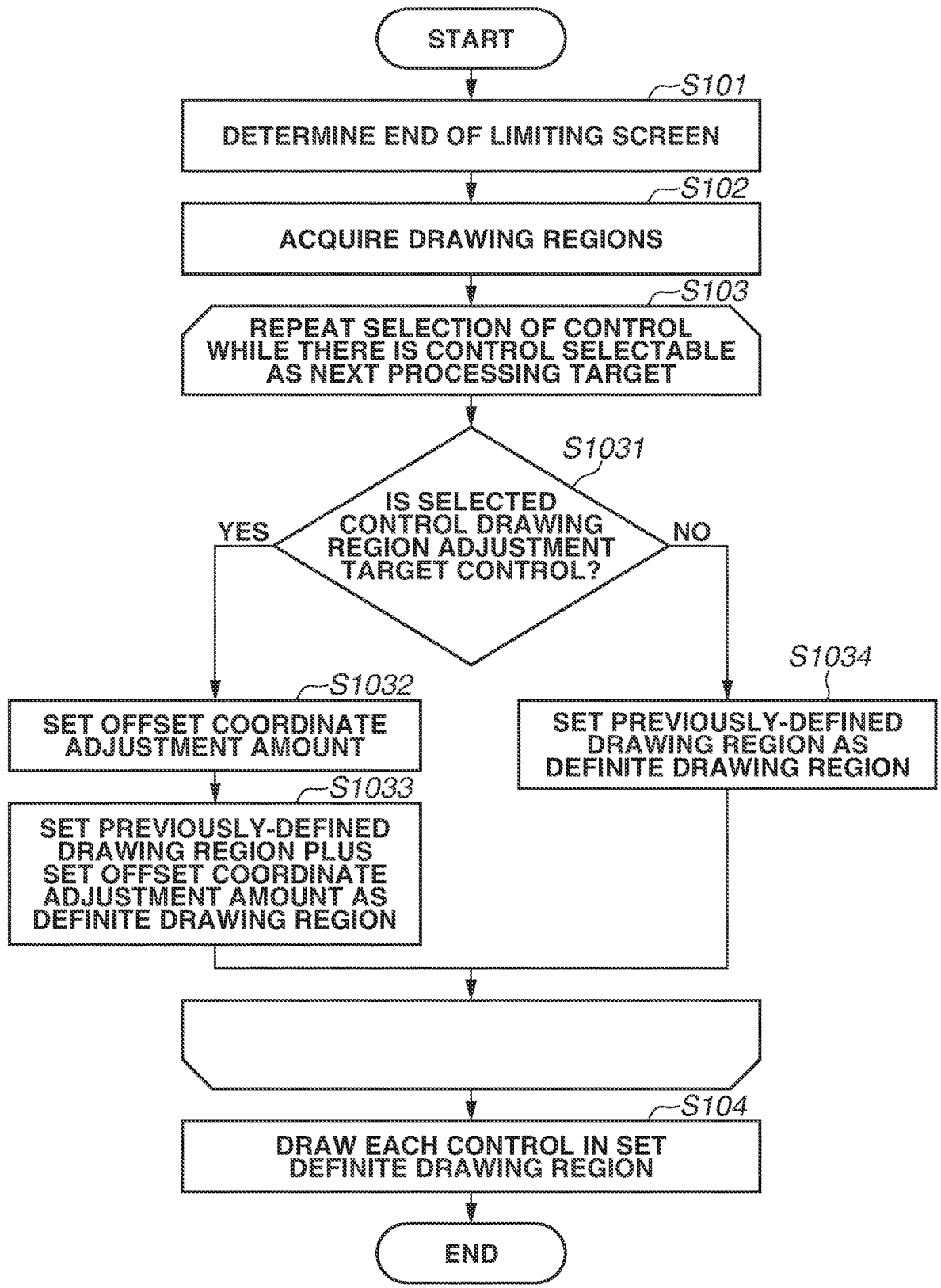
FIG. 12 is a first flowchart illustrating an example of a sequence of processing according to the first exemplary embodiment.
Figure 13:
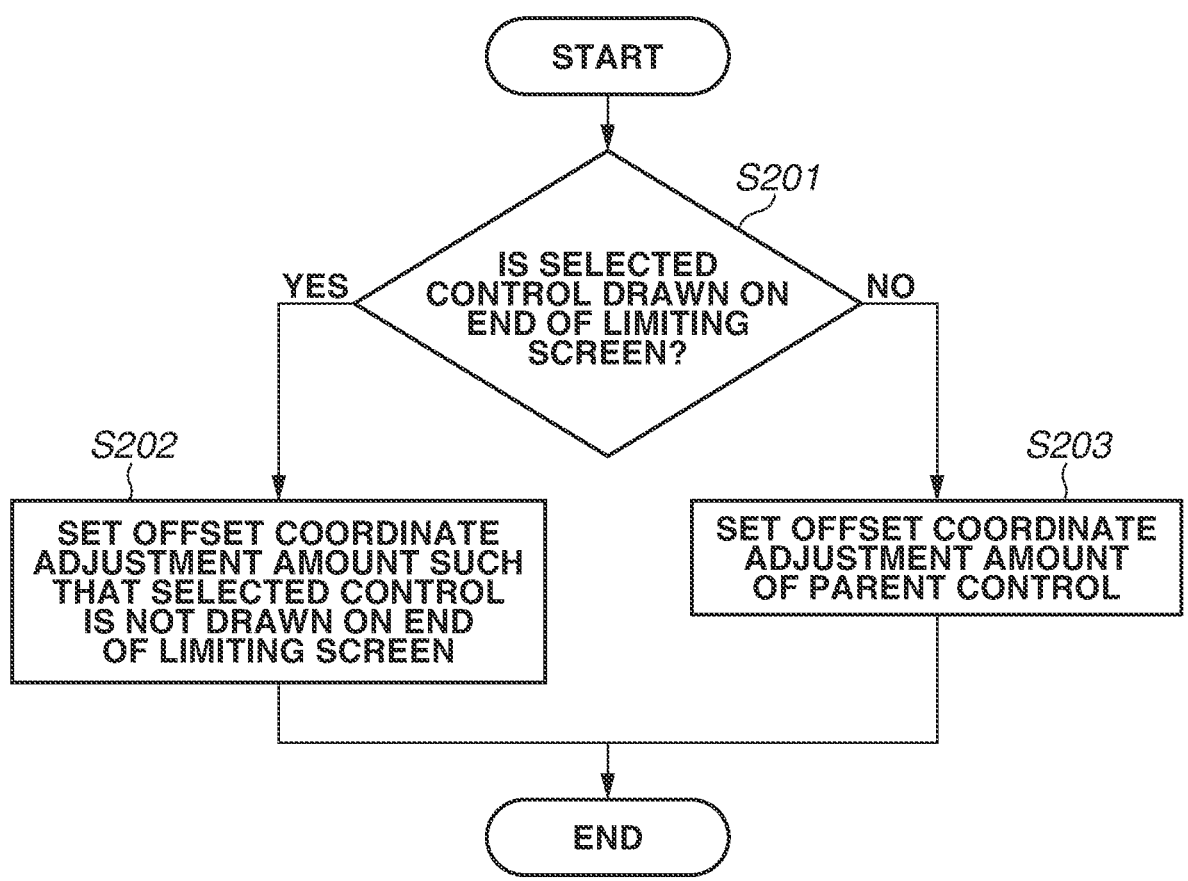
FIG. 13 is a second flowchart illustrating an example of a sequence of processing according to the first exemplary embodiment.

In the present exemplary embodiment, the process illustrated in the flowchart in FIG. 12 is started at a time point, as a start point, at which the medical image display software 100 re-draws a portion of the GUI that is detected by the re-drawing processing detection unit 101. Specific examples of the time point at which the re-drawing is performed include a time point at which the GUI of the medical image display software 100 is displayed, a time point at which the GUI is moved, a time point at which an instruction to forcibly perform re-drawing is provided by the medical image display software 100, and a time point at which an instruction to forcibly perform re-drawing is provided by the operation terminal 203. Examples of the time point at which the GUI of the medical image display software 100 is displayed include a time point at which the medical image display software 100 is started. Examples of the time point at which the GUI is moved include a time point at which the window 300, as the GUI of the medical image display software 100, is moved on the screen by the user. During the movement, re-drawing is performed at suitable time intervals. Specifically, this corresponds to an example of a determination unit configured to perform determination each time an instruction to re-draw the window or the display part is detected. In the description of the process according to the present exemplary embodiment, the situation in which the function buttons being the drawing region adjustment target controls from among the GUI of the medical image display software 100 are re-drawn will be described as an example.

There are matters that need to be determined in advance. The first matter is a control to be determined as a drawing region adjustment target control. The second matter is a screen end (hereinafter, "limiting screen end") to be determined as a screen end over which the control is not to be drawn. The third matter is a direction (hereinafter, "drawing coordinate movement direction") to be determined as a direction in which the drawing coordinate is to be moved in the case where the control is drawn over the screen end. In the present exemplary embodiment, as described above, the function buttons are determined as drawing region adjustment target controls. A derivative function button, an image thumbnail, or an examined image can be included as a drawing region adjustment target control.

In the case where a drawing region adjustment target control is drawn over the right screen end of the first display apparatus 201 or the left screen end of the second display apparatus 202, the drawing coordinate is moved rightward. Specifically, the limiting screen end is the right screen end of the first display apparatus 201 and the left screen end of the second display apparatus 202, and the drawing coordinate movement direction is the rightward direction. In the case where the selected limiting screen ends are adjacent to each other on the display coordinate, as in the description of the present exemplary embodiment, it is sufficient to determine one of the limiting screen ends to execute the process described below, so that only one of the limiting screen ends can be determined from the point of view of calculation cost. However, there can be a situation in which the limiting screen ends located close to each other on the display coordinate are not adjacent to each other. Thus, in the description of the present exemplary embodiment, two limiting screen ends are determined so that details of the process in the above-described situation are also understandable in such a case. While the two screen ends are described as the limiting screen ends in the present exemplary embodiment, other screen ends, such as the left screen end and the upper screen end of the first display apparatus 201, can be determined as the limiting screen ends. Specifically, up to four limiting screen ends can be determined if the coordinate system of the drawing region includes two dimensions, or up to six limiting screen ends can be determined if the coordinate system of the drawing region includes three dimensions.

Since the function buttons are left-justified and drawn in the function button region 301 of the medical image display software 100, it is not suitable to determine the leftward direction as the drawing coordinate movement direction. Specifically, it is not suitable to set the leftward direction as the drawing coordinate movement direction because if the leftward direction is set as the drawing coordinate movement direction, an overlap with another function button or a decrease in space from another function button can occur to make it difficult for the user to recognize the type of the control or cause erroneous operations. It is also unsuitable to set the upward direction or the downward direction as the drawing coordinate movement direction because if the upward direction or the downward direction is set as the drawing coordinate movement direction, since the limiting screen end is along the Y-axis direction in the present exemplary embodiment, the control drawing region is arranged on the screen end even after moving. Thus, it is suitable to select the drawing coordinate movement direction in the present exemplary embodiment from the rightward direction, the upper right direction, the lower right direction, the upper left direction, or the lower left direction. In the case where the drawing coordinate movement direction contains an upward direction component or a downward direction component, it is suitable to increase the region size of the function button region in the vertical direction as needed to prevent the function buttons from protruding into the thumbnail image region, etc.

In the case where the drawing coordinate movement direction contains a rightward direction component, a free area corresponding to an offset coordinate adjustment amount set in step S202 described below needs to be provided on the right side of the function button region 301. Specifically, if the free area is not large enough, a portion of the function buttons can protrude from the window 300. If the free area cannot be provided, step S101 and subsequent steps are not performed, the control that protrudes from the window 300 is hidden, and/or the size of the drawing region is changed.

In step S101, the display information acquisition unit 102 of the medical image display software 100 acquires a display coordinate and determines a limiting screen end based on the coordinates of the screen ends of the respective display apparatuses. Specifically, in the display coordinate illustrated in FIG. 7, the screen ends of the first display apparatus 201 are X=0, X=1079, Y=0, and Y=1919, and the screen ends of the second display apparatus 202 are X=1080, X=2159, Y=0, and Y=1919. As to the limiting screen ends, the coordinate of the right screen end (hereinafter, "right limiting screen end") of the first display apparatus 201 is X=1079, and the coordinate of the left screen end (hereinafter, "left limiting screen end") of the second display apparatus 202 is X=1080.

While one right limiting screen end and one left limiting screen end are determined in the present exemplary embodiment, the number of the right limiting screen end and the left limiting screen end is increased or decreased depending on the configurations of the display apparatuses, the display coordinate settings, etc.

In step S102, the drawing region acquisition unit 103 of the medical image display software 100 acquires control coordinates of controls to be re-drawn. The drawing region acquisition unit 103 calculates from the control coordinates the drawing regions of the function buttons that are drawing region adjustment target controls, and the drawing region acquisition unit 103 recognizes where to draw which function button in the display coordinate. The controls to be re-drawn can be only some of the function buttons depending on the content of a re-drawing instruction. In this situation, it is suitable to perform the processing in step S102 by treating all the function buttons that are drawing region adjustment target controls as the controls to be re-drawn, because if the drawing regions of only some of the function buttons are adjusted, the function buttons may be superimposed and drawn on another unadjusted function button.

In step S103, the drawing region determination unit 104 of the medical image display software 100 selects one control as a processing target of step S1031. A control with high drawing priority is selected as the control to be the processing target from the controls to be re-drawn. The drawing priority is an index for determining the drawing order set to each control. For example, the drawing priority of a control located in the background is higher than the drawing priority of a control located in the foreground. Specifically, in FIG. 4, the drawing priority of the window 300 is higher than the drawing priority of the function buttons. In the cases where there is no distinction of the background and the foreground between controls, the drawing priority of the control that is higher in the coordinate dependence relationship is higher than the other. Specifically, as to the function buttons that are left-justified and drawn in the function button region 301 in FIG. 4, the drawing priority of a function button located on the left is higher than the drawing priority of a function button located on the right. Specifically, if the drawing region of a function button located on the left is not determined, the drawing regions of function buttons located on the right of the function button located on the left cannot be determined, so that the priority of the function button located on the left needs to be set high to determine the drawing region first. If a control is previously selected as a processing target in step S103, the control will not be selected again unless otherwise specified. If there is no more control selectable as a processing target, step S104 is performed.

In step S1031, the drawing region determination unit 104 of the medical image display software 100 determines whether the control selected in step S103 is a drawing region adjustment target control. If the selected control is a drawing region adjustment target control, i.e., if the type of the control is a function button (YES in step S1031), step S1032 is performed. If the selected control is not a drawing region adjustment target control (NO in step S1031), step S1034 is performed. Specifically, this corresponds to an example of a changing unit configured to execute the change with respect to the display part that is predetermined and does not execute the change with respect to a display part different from the predetermined display part.

In step S1032, the drawing region determination unit 104 of the medical image display software 100 calculates and sets an offset coordinate adjustment amount of the control selected in step S103 (hereinafter, "selected control"). The offset coordinate adjustment amount refers to information about a movement amount that is set with respect to each drawing region adjustment target control and by which the drawing region is moved to prevent the drawing region adjustment target control from being drawn over the limiting screen ends. The number of dimensions of the offset coordinate adjustment amount and the unit system are similar to those of the coordinate system of the drawing region. Specifically, in the coordinate system of the present exemplary embodiment, if the offset coordinate adjustment amount of a control is set to X=10 and Y=0, the offset coordinate adjustment amount is added to the previously-defined drawing region and the drawing region of the control is moved rightward by 10 pixels and drawing is performed.

A specific process of calculating an offset coordinate adjustment amount will be described below with reference to the flowchart in FIG. 13.

In step S201, the drawing region determination unit 104 of the medical image display software 100 determines whether the selected control is drawn over the limiting screen ends. Specifically, step S201 corresponds to an example of a determination unit configured to determine whether at least a portion of a display part in a window displayed in a displayable region of the display apparatus is arranged at a position outside the displayable region. Step S201 corresponds to an example of a determination unit configured to determine whether a display part in the window is arranged over a first displayable region of the first display apparatus and a second displayable region of the second display apparatus. Step S201 corresponds to an example of a determination unit configured to determine whether the display part is arranged over the first displayable region and the second displayable region based on an end of the first displayable region or an end of the second displayable region and the position of the display part. In the present exemplary embodiment, since one right limiting screen end and one left limiting screen end are determined in step S101, the determination is performed with respect to each of the determined limiting screen ends.

Specifically, first, it is determined whether a portion other than the right end coordinate of the drawing region of the selected control is drawn on the coordinates of the right limiting screen ends determined in step S101. An offset coordinate adjustment amount of a parent control in the coordinate dependence relationship of the selected control is added to the drawing region of the selected control, and the following calculation is performed, details of which will be described below. The parent control refers to a control with the closest dependence relationship among the controls that are higher in the coordinate dependence relationship. Specifically, in FIG. 4, the left one of adjacent function buttons from among the function buttons that are left-justified and drawn in the function button region 301 is a parent control, and the parent control of the leftmost function button Fn1 is the window 300. A default value of the offset coordinate adjustment amount of each control is X=0 and Y=0, and if there is no parent control, the offset coordinate adjustment amount is X=0 and Y=0. In the coordinate dependence relationship of the medical image display software 100 in the present exemplary embodiment, the highest control is the window 300 in FIG. 4, i.e., the window 300 is the only control with no parent control. As described above in the description of step S103, the drawing priority of the parent control is higher than the drawing priority of the selected control, so that the offset coordinate adjustment amount of the parent control is already set at the time of determining the offset coordinate adjustment amount of the selected control.

In FIG. 11, in the case where the selected control is the function button Fn6, the parent control is the function button Fn5. For description, the offset coordinate adjustment amount of the function button Fn5 at this time point is X=0 and Y=0. Since the upper left of the drawing region of the function button Fn6 is (X, Y)=(960, 20) and the lower right is (X, Y)=(1159, 219), the upper left of the drawing region other than the right end coordinate of the drawing region is (X, Y)=(960, 20) and the lower right is (X, Y)=(1158, 219). The drawing region other than the right end coordinate lies on the coordinate X=1079, which is the right limiting screen end, so that it is determined that the function button Fn6 is to be drawn over the limiting screen end. Next, whether a portion other than the left end coordinate of the drawing region of the selected control is drawn on the coordinates of the left limiting screen ends determined in step S101 is determined. This will be described below with reference to FIG. 11, as in the above-described example of the case of the right limiting screen end. Since the upper left of the drawing region of the function button Fn6 is (X, Y)=(960, 20) and the lower right is (X, Y)=(1159, 219), the upper left of the drawing region other than the left end coordinate of the drawing region is (X, Y)=(961, 20) and the lower right is (X, Y)=(1159, 219). Since the drawing region other than the left end coordinate lies on the coordinate X=1080, which is the left limiting screen end, it is determined that the function button Fn6 is drawn over the limiting screen end of the second display apparatus 202. If it is determined that the selected control is drawn over the limiting screen ends (YES in step S201), step S202 is performed. If it is determined that the selected control is not drawn over the limiting screen ends (NO in step S201), step S203 is performed.

In step S202, the drawing region determination unit 104 of the medical image display software 100 sets an offset coordinate adjustment amount as the offset coordinate adjustment amount of the selected control such that the selected control is not drawn over the limiting screen end. Specifically, this corresponds to an example of a changing unit configured to change, based on a result of the determination, at least a position of the display part, a size of the display part, or a size of a region where the display part is to be arranged, in such a way that the display part is prevented from being arranged over the first displayable region and the second displayable region. If an offset coordinate adjustment amount is already set by any processing, one of the already-set offset coordinate adjustment amount and the new offset coordinate adjustment amount set in step S202 that has a larger norm is employed. Details thereof will be described below with reference to FIG. 11. In the following description, the offset coordinate adjustment amount set to the function button Fn5 is X=0 and Y=0.

The process is performed sequentially on the limiting screen ends over which the function button Fn6 is judged as being drawn in step S201, in order from left to right. First, the offset coordinate adjustment amount calculation processing is performed with respect to the right limiting screen end of the first display apparatus 201. Specifically, this corresponds to an example of an acquisition unit configured to acquire a position in which the display part is not arranged over the first displayable region and the second displayable region. The reason for processing the limiting screen ends in order from left to right is to process the limiting screen ends in order opposite to the predetermined drawing coordinate movement direction. Specifically, since the drawing coordinate movement direction is the rightward direction, the processing is performed in order from left to right. A first provisional drawing region is calculated by adding the offset coordinate adjustment amount of the function button Fn5, which is the parent control of the function button Fn6, to the drawing region of the function button Fn6. As a result, the first provisional drawing region lies on the right limiting screen end, so that a first offset coordinate adjustment amount is calculated such that the function button Fn6 is not drawn in the region from X=960, which is the left end coordinate of the drawing region of the function button Fn6, to X=1079, which is the coordinate of the right limiting screen end. Specifically, X=1079−960+1=120 and Y=0 are calculated as the first offset coordinate adjustment amount. Next, the offset coordinate adjustment amount calculation processing is performed on the left limiting screen end of the second display apparatus 202. The second provisional drawing region obtained by adding the first offset coordinate adjustment amount to the first provisional drawing region does not lie on the left limiting screen end, so that X=120 and Y=0, which remain unchanged from the first offset coordinate adjustment amount, are calculated as the second offset coordinate adjustment amount. The offset coordinate adjustment amount calculated lastly in the above-described processing, i.e., second offset coordinate adjustment amount, is set as the offset coordinate adjustment amount of the function button Fn6.

There can be a case in which the regions of the first display apparatus 201 and the second display apparatus 202 are not adjacent to each other with respect to the display coordinates managed by the operation terminal 203, which is a different situation from the present case. Specifically, the right limiting screen end of the first display apparatus 201 and the left limiting screen end of the second display apparatus 202 are not adjacent to each other. In this case, the second offset coordinate adjustment amount is a value with a larger norm than that of the first offset coordinate adjustment amount.

If the offset coordinate adjustment amount in step S202 is maintained, the drawing region of the function button Fn6 is set next to the limiting screen end in subsequent step S1033. If a margin needs to be adjusted such that the function button Fn6 is not drawn next to the limiting screen end, the X-component of the offset coordinate adjustment amount of the function button Fn6 can be increased to set a margin between the function button Fn6 and the limiting screen end.

In step S203, the drawing region determination unit 104 of the medical image display software 100 sets, as the offset coordinate adjustment amount of the selected control, the same value as the offset coordinate adjustment amount set to the parent control in the coordinate dependence relationship of the selected control.

The following is a continuation of the description of the process illustrated in the flowchart in FIG. 12.

In step S1033, the drawing region determination unit 104 of the medical image display software 100 sets, to the selected control, a definite drawing region obtained by adding the offset coordinate adjustment amount set to the selected control in step S1032 to the previously-defined drawing region of the selected control. The definite drawing region refers to a drawing region in which the control is to be drawn on the GUI.

In step S1034, the drawing region determination unit 104 of the medical image display software 100 sets the previously-defined drawing region of the selected control as a definite drawing region.

In step S104, the screen display unit 105 of the medical image display software 100 re-draws the controls based on the definite drawing regions set to the respective controls. The re-drawn GUI is displayed on the display apparatuses by the display control unit 36. In this way, the user can check the re-drawn GUI on the display apparatuses.

As described above, the medical image display software of the present exemplary embodiment prevents each control of a GUI from being drawn over the ends of displayable regions of display apparatuses to make it easier for the user to recognize the type of the control so that operation delays and erroneous operations are prevented.

Medical image display software for use in radiologic interpretations that includes a GUI drawing method and a program according to a second exemplary embodiment of the present invention will now be described.

The terms that are necessary to describe the present exemplary embodiment are the same as those in the first exemplary embodiment.

The present exemplary embodiment is similar to the first exemplary embodiment in many points, so the present exemplary embodiment will be described with reference to the drawings in the first exemplary embodiment.

Figure 14:
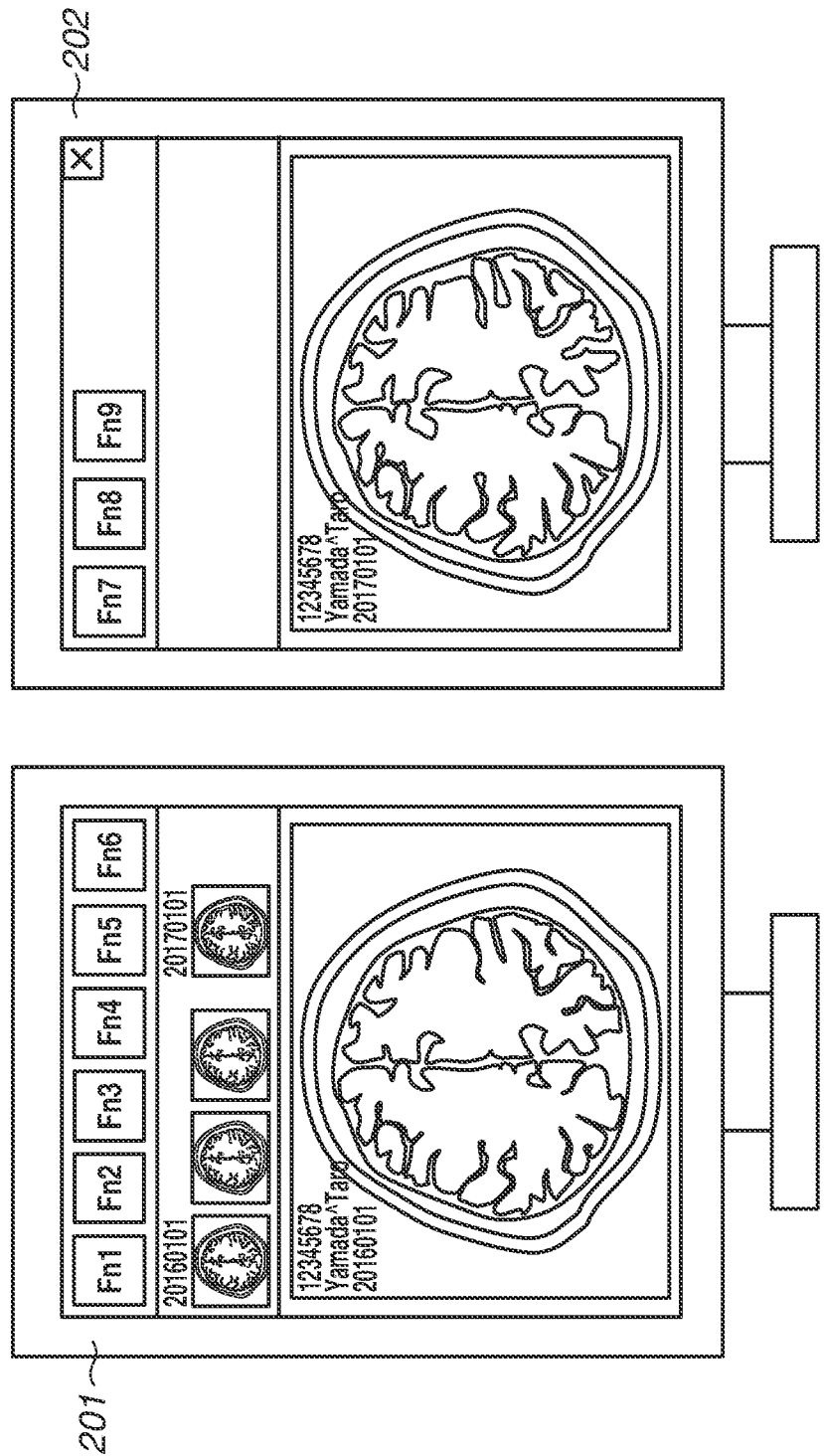
FIG. 14 illustrates an example of a state of medical image display software according to a second exemplary embodiment.
Figure 15:
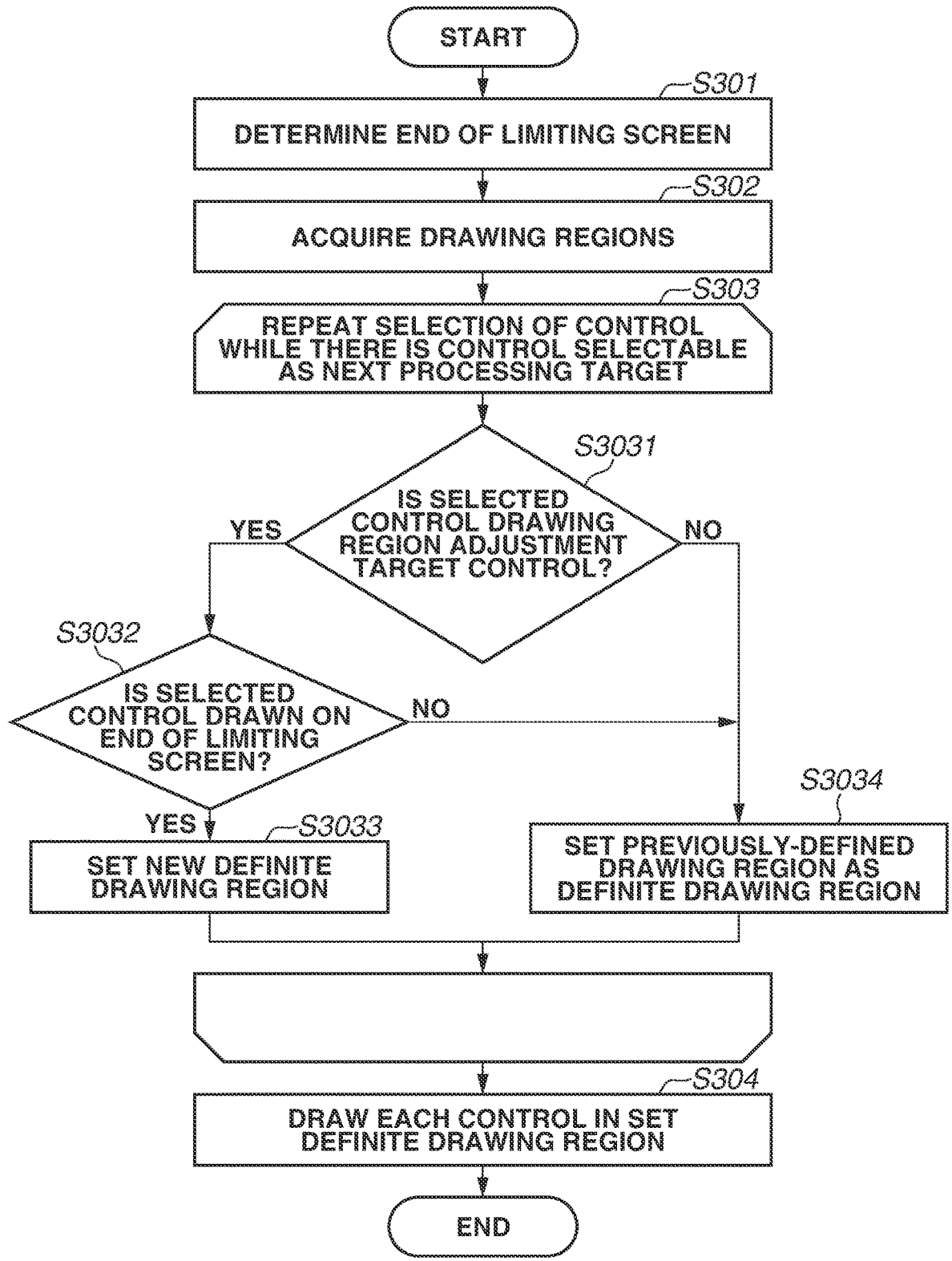
FIG. 15 is a flowchart illustrating an example of a sequence of processing according to the second exemplary embodiment.

In the first exemplary embodiment, the offset coordinate adjustment amount is set to prevent the drawing region adjustment target controls from being drawn over the limiting screen frames, and the drawing region adjustment target controls are moved. In the second exemplary embodiment, as illustrated in FIG. 14, the size of the drawing region of one or more drawing region adjustment target controls is adjusted, i.e., enlarged or reduced, such that the drawing region adjustment target controls do not lie on the limiting screen frames. Specifically, the processing corresponding to steps S1032 and S1033 in FIG. 12 in the first exemplary embodiment corresponds to the processing of adjusting the size of the drawing region as illustrated in FIG. 15.

A process of the present exemplary embodiment will be described below with reference to the flowchart in FIG. 15.

There are matters that need to be determined in advance. The first matter is a control to be determined as a drawing region adjustment target control. The second matter is a screen end (hereinafter, "limiting screen end" as in the first exemplary embodiment) to be determined as a screen end over which the control is not to be drawn. The third matter is whether to reduce or enlarge the size in the case where the drawing region adjustment target controls are drawn over the limiting screen frames (hereinafter, "drawing region size adjustment method"). In the present exemplary embodiment, the function buttons are determined as drawing region adjustment target controls. The drawing region size adjustment method is set such that the size is reduced if a drawing region adjustment target control is drawn over the right screen end of the first display apparatus 201 or over the left screen end of the second display apparatus 202. In the case where the drawing region size adjustment method is set to enlarge the size, it is suitable to enlarge the region size of the function button region as needed to prevent the function button from protruding into the thumbnail image region, etc. In the case where the drawing region size adjustment method is set to reduce the size, it is suitable to reduce the region size of the function button region as needed to prevent the margin in the vicinity of the function buttons from being excessively enlarged. If the function buttons are enlarged, the free area on the right side of the function button region is reduced, so that a portion of the function buttons may protrude from the window 300 if the free area is insufficient. If the free area cannot be provided, step S301 and subsequent steps are not performed or the control that protrudes from the window 300 is hidden. The region size of the function button region can be enlarged as needed while the function buttons are arranged in a plurality of lines. Specifically, if a drawing region adjustment target control protrudes from the limiting screen end, the function buttons drawn in a single line are drawn in two lines, and the drawing region adjustment target control is drawn in the second line.

Steps S301, S302, S303, S3031, S3034, and S304 are similar to steps S101, S102, S103, S1031, S1034, and S104 in the flowchart of the first exemplary embodiment in FIG. 12.

In step S3032, the drawing region determination unit 104 of the medical image display software 100 determines whether the control (hereinafter, "selected control") selected in step S303 is drawn over the limiting screen ends. In the present exemplary embodiment, since one right limiting screen end and one left limiting screen end are determined in step S301, the determination is performed with respect to each of the determined limiting screen ends.

Specifically, first, it is determined whether a portion other than the right end coordinate of the drawing region of the selected control is drawn on the coordinates of the right limiting screen ends determined in step S301. In FIG. 11, the upper left of the drawing region of the function button Fn6 is (X, Y)=(960, 20) and the lower right is (X, Y)=(1159, 219). Specifically, the upper left of the drawing region other than the right end coordinate of the drawing region is (X, Y)=(960, 20) and the lower right is (X, Y)=(1158, 219). Since the drawing region other than the right end coordinate is on the coordinate X=1079, which is the right limiting screen end, it is determined that the function button Fn6 is drawn over the limiting screen end. Next, whether a portion other than the left end coordinate of the drawing region of the selected control is drawn on the coordinates of the left limiting screen ends that are determined in step S301 is determined. In FIG. 11, as in the example of the case of the right limiting screen end, the upper left of the drawing region of the function button Fn6 is (X, Y)=(960, 20) and the lower right is (X, Y)=(1159, 219). Specifically, the upper left of the drawing region other than the left end coordinate of the drawing region is (X, Y)=(961, 20) and the lower right is (X, Y)=(1159, 219). Since the drawing region other than the left end coordinate is on the coordinate X=1080, which is the left limiting screen end, it is determined that the function button Fn6 is drawn over the limiting screen end, as already determined. If it is determined that the selected control is drawn over the limiting screen end (YES in step S3032), step S3033 is performed. If it is determined that the selected control is not drawn over the limiting screen end (NO in step S3032), step S3034 is performed.

In step S3033, the drawing region determination unit 104 of the medical image display software 100 sets the selected control and a definite drawing region. Specifically, this corresponds to an example of a changing unit configured to change, based on a result of the determination, at least a position of the display part, a size of the display part, or a size of a region where the display part is to be arranged, in such a way that the display part is prevented from being arranged over the first displayable region and the second displayable region. The setting of the definite drawing region is executed to change the drawing region size of the drawing region adjustment target controls displayed on the display apparatus on which the upper left coordinate of the drawing region of the selected control exists. The definite drawing region is a drawing region set to prevent each drawing region adjustment target control from being drawn over the limiting screen end and is coordinate information about the drawing region for enlarging or reducing the size thereof. For example, there is a case in which the upper left of the drawing region of a control is (X, Y)=(0, 0) and the lower right is (X, Y)=(10, 10) in the coordinate system of the present exemplary embodiment. If the upper left of a new drawing region of the control is (X, Y)=(0, 0) and the lower right is (X, Y)=(20, 20), the drawing is performed while the upper left coordinate of the control remains unchanged and the size is doubled in the vertical direction and also doubled in the horizontal direction. In the case where the function button Fn6 lies on the limiting screen end as illustrated in FIG. 11, if the right end coordinate of the definite drawing region of the function button Fn6 is adjusted to the right limiting screen end of the first display apparatus 201, the reduction of the function buttons Fn1 to Fn6 is minimized.

Specifically, since the right end drawing region of the function button Fn6 is X=1159 and the coordinate of the right limiting screen end is X=1079, the difference is Diff=1159−1079=80. Amounts by which the respective six function buttons, the function buttons Fn1 to Fn6, are to be reduced respectively are calculated. As a result of calculation, Diff/6=80/6≈13.3 pixels is obtained. Since the pixels are expressed by a natural number, the number of pixels can be 14. Accordingly, the definite drawing region is reduced to be smaller by 14 pixels than the width of the original drawing region while the margins between the function buttons remain unchanged. In this way, the six function buttons, the function buttons Fn1 to Fn6, are set to be left-justified with respect to the function button region 301. If an additional margin is needed between the function button Fn6 and the right limiting screen end of the first display apparatus 201, the amount of 14 pixels can be increased to a greater value.

In step S304, the screen display unit 105 of the medical image display software 100 re-draws the controls based on the definite drawing regions set to the respective controls. The re-drawn GUI is displayed on the display apparatuses by the display control unit 36. In this way, the user can check the re-drawn GUI on the display apparatuses.

As described above, the medical image display software of the present exemplary embodiment prevents each control of a GUI from being drawn over the ends of displayable regions of display apparatuses to make it easier for the user to recognize the type of the control so that operation delays and erroneous operations are prevented. Execution of unnecessary functions due to erroneous operations is reduced so that the processing load on the control unit 37 is reduced.

A first modified example will be described below. In the first exemplary embodiment, the coordinates of the drawing regions of the drawing region adjustment target controls are changed, i.e., the drawing region adjustment target controls are moved, so that the drawing region adjustment target controls are controlled not to be arranged over the limiting screen frames. In the second exemplary embodiment, the size of the drawing region of the drawing region adjustment target controls is enlarged or reduced such that the drawing region adjustment target controls are controlled not to be arranged over the limiting screen frames. Specifically, the medical image display software 100 enlarges or reduces the size of the function buttons. The drawing region adjustment target control region (e.g., function button region 301) is enlarged or reduced so that the drawing region adjustment target controls are controlled not to be arranged over the limiting screen frames.

CT apparatuses and MRI apparatuses output a plurality of cross-sectional images (also referred to as "sliced images"). In the cases where the medical image display software displays the plurality of cross-sectional images as a single series, for example, the user operates a mouse wheel to switch the display of the cross-sectional images. This is a paging function.

As in the first and second exemplary embodiments, in the cases of drawing cross-sectional images as examined images on the examined image region 303, various changes are executed so that the cross-sectional images are not drawn over the limiting screen frames. At this time, if the display of a cross-sectional image on which the various changes are executed is switched by the paging function, the medical image display software desirably executes the same changes on the newly displayed cross-sectional image as the changes executed on the cross-sectional image that is previously displayed before the switch. Specifically, in the case where the drawing coordinate of the cross-sectional image before the switch is changed, it is desirable to change the drawing coordinate of the cross-sectional image after the switch to the same coordinate. It is desirable to apply the enlargement ratio (size) of the drawing region of the cross-sectional image before the switch to the enlargement ratio of the drawing region of the cross-sectional image after the switch. It is desirable to apply the enlargement ratio of the examined image region 303 in which the cross-sectional image before the switch is drawn to the enlargement ratio of the examined image region 303 in which the cross-sectional image after the switch is drawn.

In this way, even if the display of the cross-sectional image is switched by the paging function, the cross-sectional image is displayed in the same position as the position before the switch. The cross-sectional image is displayed at the same enlargement ratio as the enlargement ratio applied before the switch. The examined image region in which the cross-sectional image is drawn is displayed at the same enlargement ratio as the enlargement ratio applied before the switch.

In the cases where the display of thumbnail images is switchable by the paging function, a similar advantage is produced by executing processing similar to the above-described processing executed on the cross-sectional image.

The foregoing processing corresponds to an example of the changing unit configured to execute on a second medical image the same change as the change executed with respect to a first medical image in a case where the first medical image is switched to the second medical image.

A second modified example will be described below. In the first exemplary embodiment, the coordinates of the drawing regions of the drawing region adjustment target controls are changed, i.e., the drawing region adjustment target controls are moved, so that the drawing region adjustment target controls are controlled not to be arranged over the limiting screen frames. In the second exemplary embodiment, the size of the drawing region of the drawing region adjustment target controls is enlarged or reduced such that the drawing region adjustment target controls are controlled not to be arranged over the limiting screen frames. Specifically, the medical image display software 100 enlarges or reduces the size of the function buttons. The drawing region adjustment target control region (e.g., function button region 301) is enlarged or reduced so that the drawing region adjustment target controls are controlled not to be arranged over the limiting screen frames.

The medical image display software needs to only execute at least one of the changes, not all the changing methods. The medical image display software can execute all the changes or a combination of some of the changes.

As an alternative changing method, the drawing region adjustment target controls that are drawn over the limiting screen frames can be hidden and can be combined together as a single expand button or a plurality of expand buttons. Specifically, if a selection that is made with respect to the expand button is received, the drawing region adjustment target controls that have been hidden are displayed, for example, in the form of pop-ups.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2017-196055, filed Oct. 6, 2017, which is hereby incorporated by reference herein in its entirety.

What is claimed is:

1. An information processing apparatus configured to display a window including a plurality of display parts in each of a plurality of regions over a first displayable region of a first display apparatus and a second displayable region of a second display apparatus, the information processing apparatus comprising:
   a memory storing a program; and
   one or more processors which, by executing the program, function as:
   a determination unit configured to determine whether a first display part in the window is arranged over the first displayable region of the first display apparatus and the second displayable region of the second display apparatus; and
   a changing unit configured to change, by using a position of the first display part and a position of a second display part in a region where the first display part is to be arranged based on a result of the determination, at least the position of the first display part and the position of the second display part, and a size of the first display part and a size of the second display part, such that the first display part and the second display part are prevented from being arranged over the first displayable region and the second displayable region, in a case where the determination unit determines that the first display part is arranged over the first displayable region and the second displayable region.

2. The information processing apparatus according to claim 1, wherein the determination unit determines whether the first display part is arranged over the first displayable region of the first display apparatus and the second displayable region of the second display apparatus based on an end of the first display part in the first displayable region of the first display apparatus or an end of second display part in the second displayable region of the second display apparatus, and the position of the first display part and the second display part.

3. The information processing apparatus according to claim 1, wherein, the one or more processor which, by executing the program, further function as:
   an acquisition unit configured to acquire a position at which the first display part and the second display part are not arranged over the first displayable region and the second displayable region,
   wherein the changing unit changes the position of the first display part and the second display part based on the acquired position.

4. The information processing apparatus according to claim 1, wherein the changing unit changes the position of the first display part based on the position of the first display part and a position of another display part different from the first display part.

5. The information processing apparatus according to claim 1, wherein the changing unit executes any of the changes in a case where the determination unit determines that the first display part is arranged over the first displayable region of the first display apparatus and the second displayable region of the second display apparatus.

6. The information processing apparatus according to claim 1, wherein the changing unit does not execute the change in a case where the determination unit determines that the first display part is not arranged over the first displayable region of the first display apparatus and the second displayable region of the second display apparatus.

7. The information processing apparatus according to claim 1, wherein the changing unit executes any of the changes with respect to the first display part and the second display part that is a predetermined first display part and the second display part and does not execute the change with respect to a first display part and the second display part different from the predetermined first display part and the second display part.

8. The information processing apparatus according to claim 1,
   wherein the display parts in each of the plurality of regions includes a plurality of medical images, and
   wherein, in a case where a first medical image is switched to a second medical image, the changing unit executes, on the second medical image, a same change as a change executed with respect to the first medical image.

9. The information processing apparatus according to claim 1, wherein the determination unit performs the determination each time an instruction to re-draw the window or the display part in each of the plurality of region is detected.

10. The information processing apparatus according to claim 1, wherein the display part is a graphical user interface (GUI) that executes a predetermined function.

11. An information processing method of displaying a window including a plurality of display parts in each of a plurality of regions over a first displayable region of a first display apparatus and a second displayable region of a second display apparatus, the information processing method comprising:
    determining whether a first display part in the window is arranged over the first displayable region of the first display apparatus and the second displayable region of the second display apparatus; and
    changing, by using a position of the first display part and a position of a second display part in a region where the first display part is to be arranged based on a result of the determination, at least the position of the first display part and the position of the second display part, and a size of the first display part and a size of the second display part, such that the first display part and the second display part are prevented from being arranged over the first displayable region and the second displayable region, in a case where the determination unit determines that the first display part is arranged over the first displayable region and the second displayable region.

12. A non-transitory computer-readable storage medium storing a computer program that causes a computer to execute an information processing method of displaying a window including a plurality of display parts in each of a plurality of regions over a first displayable region of a first display apparatus and a second displayable region of a second display apparatus, the information processing method comprising:
    determining whether a first display part in the window is arranged over the first displayable region of the first display apparatus and the second displayable region of the second display apparatus; and
    changing, by using a position of the first display part and a position of a second display part in a region where the first display part is to be arranged based on a result of the determination, at least the position of the first display part and position of the the second display part, and a size of the first display part and a size of the second display part, such that the first display part and the second display part are prevented from being arranged over the first displayable region and the second displayable region, in a case where the determination unit determines that the first display part is arranged over the first displayable region and the second displayable region.

\* \* \* \* \*